(12) United States Patent
Li et al.

(10) Patent No.: US 12,000,774 B2
(45) Date of Patent: Jun. 4, 2024

(54) GAS ANALYZER

(71) Applicant: THERMO ENVIRONMENTAL INSTRUMENTS LLC, Franklin, MA (US)

(72) Inventors: Yongquan Li, Schenactady, NY (US); Brian Chia, Natick, MA (US); Robert Bailey, Bellingham, MA (US)

(73) Assignee: Thermo Environmental Instruments LLC, Franklin, MA (US)

( * ) Notice: Subject to any disclaimer, the term of this patent is extended or adjusted under 35 U.S.C. 154(b) by 0 days.

(21) Appl. No.: 17/823,200

(22) Filed: Aug. 30, 2022

(65) Prior Publication Data

US 2023/0078598 A1    Mar. 16, 2023

Related U.S. Application Data (60) Provisional application No. 63/261,224, filed on Sep. 15, 2021.

(51) Int. Cl.
  *G01N 21/05*   (2006.01)
  *G01N 21/31*   (2006.01)
  *G01N 33/00*   (2006.01)

(52) U.S. Cl.
  CPC ......... *G01N 21/31* (2013.01); *G01N 33/0027* (2013.01); *G01N 2201/062* (2013.01); *G01N 2201/0636* (2013.01)

(58) Field of Classification Search
  CPC ............... G01N 21/31; G01N 33/0027; G01N 2201/062; G01N 2201/0636
  See application file for complete search history.

(56) References Cited

U.S. PATENT DOCUMENTS

| | | | |
|---|---|---|---|
| 6,791,689 B1 | 9/2004 | Weckström | |
| 10,488,258 B2* | 11/2019 | Keller | G01N 21/031 |
| 10,684,215 B2* | 6/2020 | Birks | G01N 21/5907 |
| 11,150,130 B2 | 10/2021 | Sabry et al. | |
| 2002/0185603 A1* | 12/2002 | Daly | G01N 21/031 |
| | | | 356/246 |
| 2004/0090628 A1 | 5/2004 | Ershov et al. | |

(Continued)

FOREIGN PATENT DOCUMENTS

| | | | | |
|---|---|---|---|---|
| KR | 20210097064 A | * | 8/2021 | ......... G01N 15/0656 |
| WO | WO-2020180972 A1 | | 9/2020 | |

OTHER PUBLICATIONS

"Basic Properties of Mirrors—Introduction to Mirrors," by Kenneth R. Spring, Thomas J. Fellers, and Michael W. Davidson (Year: 2023).*

(Continued)

*Primary Examiner* — Uzma Alam
*Assistant Examiner* — Chad Andrew Reverman
(74) *Attorney, Agent, or Firm* — William R. McCarthy, III (57) ABSTRACT

An embodiment of a gas analyzer is described that comprises a light source configured to produce a substantially collimated first beam with a diverging angle of less than about 15 degrees; a gas cell comprising an inlet configured to introduce a gas into the gas cell, an outlet configured to remove the gas from the gas cell, and a plurality of mirrors (Continued)

configured to reflect the substantially collimated first beam within the gas cell; and a detector configured to generate a signal in response to the substantially collimated first beam.

16 Claims, 6 Drawing Sheets

(56) References Cited

U.S. PATENT DOCUMENTS

| | | | |
|---|---|---|---|
| 2009/0128819 A1 | 5/2009 | Van Kesteren et al. | |
| 2009/0302230 A1* | 12/2009 | Birks | G01N 33/0024 |
| | | | 250/373 |
| 2011/0093215 A1* | 4/2011 | Zhou | G01N 21/3504 |
| | | | 702/24 |
| 2016/0084757 A1 | 3/2016 | Miron | |
| 2016/0325284 A1* | 11/2016 | Camillo | B01L 3/50851 |
| 2016/0327479 A1* | 11/2016 | Feitisch | G01N 21/3504 |
| 2018/0011003 A1* | 1/2018 | Baum | G01N 21/031 |
| 2018/0156718 A1 | 6/2018 | Fleisher et al. | |
| 2019/0113442 A1* | 4/2019 | Shibuya | G01N 21/59 |
| 2019/0226987 A1* | 7/2019 | Birks | G01N 21/49 |
| 2019/0317067 A1 | 10/2019 | Heffels et al. | |
| 2019/0355601 A1* | 11/2019 | Danen | G02B 27/0012 |
| 2020/0030515 A1* | 1/2020 | Merchant | A61B 5/02427 |
| 2020/0049560 A1* | 2/2020 | Mun | G01N 21/67 |
| 2021/0223527 A1* | 7/2021 | Meyer | G02B 21/125 |
| 2021/0247300 A1* | 8/2021 | Dattner | G01N 21/27 |
| 2021/0247301 A1* | 8/2021 | Baker | G01N 33/487 |

OTHER PUBLICATIONS

"Ultraviolet (UV) Radiation," University Corporation for Atmospheric Research (UCAR), 2017 (Year: 2017).*

Collimated Beams Encyclopedia Entry, RP Photonics Encyclopedia, Dr. Rüdiger Paschotta (Year: 2023).*

"Tour of the Electromagnetic Spectrum: Visible Light," National Aeronautics and Space Administration, Science Mission Directorate, Aug. 10, 2016 (Year: 2016).*

Birks J.W., et al., "Folded Tubular Photometer for Atmospheric Measurements of NO2 and NO," Atmospheric Measurement Techniques, 2018, vol. 11, pp. 2821-2835.

Khan S., et al., "Gas Detection Using Portable Deep-UV Absorption Spectrophotometry: A Review," Sensors, 2019, vol. 19, 5210, 31 pages.

PCT/US2022/075636, International Search Report and Written Opinion, Nov. 2, 2022, 8 pages.

* cited by examiner

GAS ANALYZER

CROSS-REFERENCE TO RELATED APPLICATIONS

This application claims priority to U.S. application No. 63/261,224 filed Sep. 15, 2021, which disclosure is herein incorporated by reference in its entirety.

FIELD OF THE INVENTION

The present invention is generally directed to a system and method enabled to measure the level of a component gas present in a sample.

BACKGROUND

It is generally appreciated that Nitrogen dioxide ($NO_2$) is a pollution gas regulated by US Environmental Protection Agency (EPA) for ambient air quality. One of EPA certified $NO_2$ measurement methods includes chemiluminescence gas measurement technology that is an indirect monitoring approach, often overestimating $NO_2$ concentrations.

In some applications, a direct measurement approach based on Beer's law is employed to measure the degree of UV absorption of a sample gas in a long pass length gas cell (e.g. a long pass length is desirable to achieve a high detection sensitivity). For example, either single pass or bulky multiple pass gas cells have been used for UV absorption photometers. However, the gas cells used are not feasible for use in "portable" gas analyzers without sacrificing sensitivity and response time. For example, traditional gas analyzers are typically too large and heavy for a single user to carry while operating the analyzer.

Further, previous analyzers have employed divergent light sources that produce a substantial amount of light scattering within the gas cell that generates a significant degree of interference signal from water (e.g. from the walls of the gas cell). These light sources also tend to degrade over time, resulting in short lifetime, and are temperature sensitive, exhibiting a significant level of instability as the ambient temperature fluctuates.

Therefore, there continues to be a need for an improved configuration of gas analyzer that is smaller than existing analyzers, as well as an analyzer that provides a more accurate and stable alternative.

SUMMARY

Systems, methods, and products to address these and other needs are described herein with respect to illustrative, non-limiting, implementations. Various alternatives, modifications and equivalents are possible.

An embodiment of a gas analyzer is described that comprises a light source configured to produce a substantially collimated first beam with a small diverging angle; a gas cell comprising an inlet configured to introduce a gas into the gas cell, an outlet configured to remove the gas from the gas cell, a first lens, a plurality of mirrors configured to reflect the substantially collimated first beam within the gas cell, and a second lens; and a detector configured to generate a signal in response to the substantially collimated first beam.

In some cases, each of the mirrors is configured to re-focus the reflected substantially collimated first beam and each of the mirrors may comprise a dielectric coating configured to provide greater than 99% reflectivity of the substantially collimated first beam. Further, in some cases an energy level of the substantially collimated first beam at the detector is substantially equal to an energy level of the substantially collimated first beam produced by the light source.

Also, in some implementations, the substantially collimated first beam comprises a band width of about 10 nm and may sometimes comprise a peak value of about 405 nm. In the same or alternative implementations, the substantially collimated first light beam may be reflected from the mirrors about 20 times in the gas cell, where the gas cell may include a pass line distance of about 2 meters.

Additionally, the gas analyzer may further include a reference sensor positioned adjacent to the light source, wherein the reference sensor detects a second beam from the light source, where the light source may produce the second beam in an opposite direction from the substantially collimated first beam. In some cases, the second beam comprises a small level of energy compared to a level of energy of the first beam.

The gas analyzer may also include a processing system configured to compensate for variation in the substantially collimated first beam using a signal from the reference sensor, where the variation may be caused by temperature fluctuation. In such a situation the gas analyzer may include a thermo electric cooler, where the processing system provides instruction to the thermo electric cooler to compensate for the temperature fluctuation. In some cases, the processing system maintains range of temperature around a set temperature that can be selectable or may include a set temperature of about 25° C. Further, the range of temperature may be about 0.1 Kelvin.

Further, the set temperature may comprise an ambient temperature of the environment outside of the gas analyzer, where the gas analyzer may include a temperature sensor configured to detect the ambient temperature.

In some implementations, the light source comprises an LED. The first lens may also be configured to focus the first beam so that diverging angle remains substantially within a reflective area of each of the mirrors. The second lens may also be configured to produce a focal point on an active area of the detector to maximize the collection efficiency of light. Further, the small diverging angle may be less than about 15 degrees.

The above embodiments and implementations are not necessarily inclusive or exclusive of each other and may be combined in any manner that is non-conflicting and otherwise possible, whether they are presented in association with a same, or a different, embodiment or implementation. The description of one embodiment or implementation is not intended to be limiting with respect to other embodiments and/or implementations. Also, any one or more function, step, operation, or technique described elsewhere in this specification may, in alternative implementations, be combined with any one or more function, step, operation, or technique described in the summary. Thus, the above embodiment and implementations are illustrative rather than limiting.

BRIEF DESCRIPTION OF THE DRAWINGS

The above and further features will be more clearly appreciated from the following detailed description when taken in conjunction with the accompanying drawings. In the drawings, like reference numerals indicate like structures, elements, or method steps and the leftmost digit of a reference numeral indicates the number of the figure in which the references element first appears (for example, element 110 appears first in FIG. 1). All of these conventions, however, are intended to be typical or illustrative, rather than limiting.

FIG. 1 is a functional block diagram of one embodiment of a gas analyzer instrument in communication with a computer.

Like reference numerals refer to corresponding parts throughout the several views of the drawings.

DETAILED DESCRIPTION OF EMBODIMENTS

As will be described in greater detail below, embodiments of the described invention include a gas cell configured for accurate measurement of a level of a component gas present in a sample.

Figure 1:
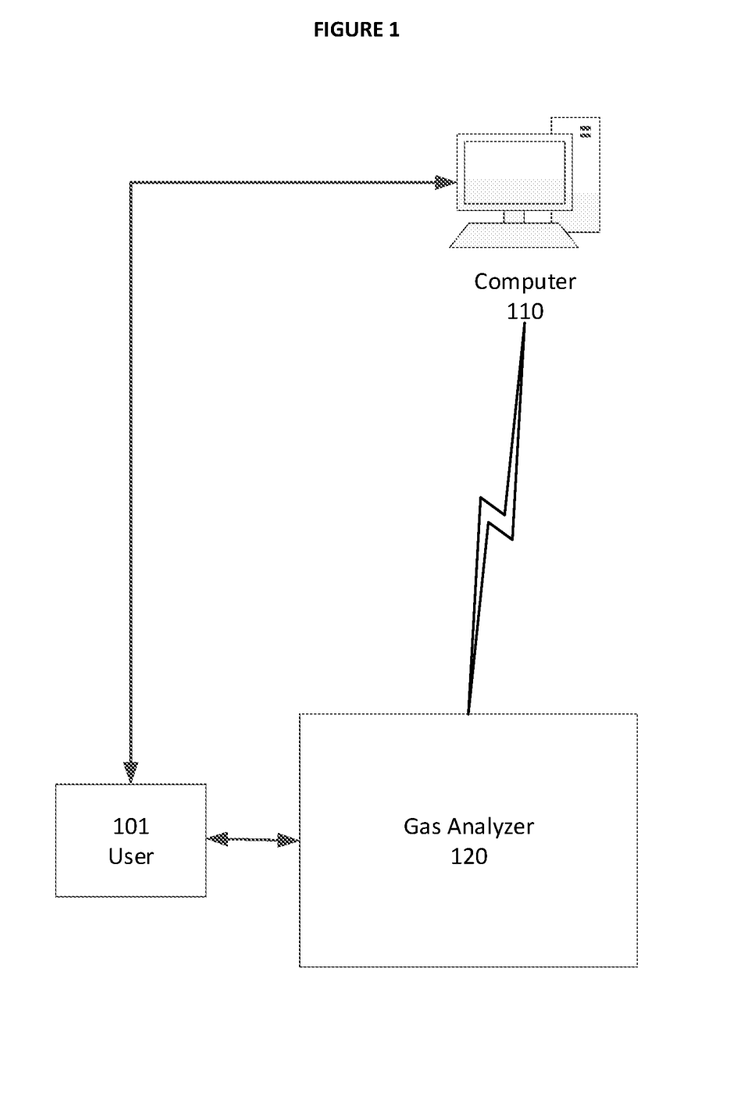

FIG. 1 provides a simplified illustrative example of user 101 capable of interacting with computer 110 and gas analyzer 120. Embodiments of gas analyzer 120 may include a variety of commercially available gas analyzers. For example, gas analyzer 120 may include the iQ series of gas analyzer instruments available from Thermo Fisher Scientific. FIG. 1 also illustrates a network connection between computer 110 and gas analyzer 120, however it will be appreciated that FIG. 1 is intended to be exemplary and additional or fewer network connections may be included. Further, the network connection between the elements may include "direct" wired or wireless data transmission (e.g. as represented by the lightning bolt) as well as "indirect" communication via other devices (e.g. switches, routers, controllers, computers, etc.), and therefore the example of FIG. 1 should not be considered as limiting.

Computer 110 may include any type of computing platform such as a workstation, a personal computer, a tablet, a "smart phone", one or more servers, compute cluster (local or remote), or any other present or future computer or cluster of computers. Computers typically include known components such as one or more processors, an operating system, system memory, memory storage devices, input-output controllers, input-output devices, and display devices. It will also be appreciated that more than one implementation of computer 110 may be used to carry out various operations in different embodiments, and thus the representation of computer 110 in FIG. 1 should not be considered as limiting.

In some embodiments, computer 110 may employ a computer program product comprising a computer usable medium having control logic (e.g. computer software program, including program code) stored therein. The control logic, when executed by a processor, causes the processor to perform some or all of the functions described herein. In other embodiments, some functions are implemented primarily in hardware using, for example, a hardware state machine. Implementation of the hardware state machine so as to perform the functions described herein will be apparent to those skilled in the relevant arts. Also in the same or other embodiments, computer 110 may employ an internet client that may include specialized software applications enabled to access remote information via a network. A network may include one or more of the many types of networks well known to those of ordinary skill in the art. For example, a network may include a local or wide area network that may employ what is commonly referred to as a TCP/IP protocol suite to communicate. A network may include a worldwide system of interconnected computer networks that is commonly referred to as the internet, or could also include various intranet architectures. Those of ordinary skill in the related art will also appreciate that some users in networked environments may prefer to employ what are generally referred to as "firewalls" (also sometimes referred to as Packet Filters, or Border Protection Devices) to control information traffic to and from hardware and/or software systems. For example, firewalls may comprise hardware or software elements or some combination thereof and are typically designed to enforce security policies put in place by users, such as for instance network administrators, etc.

As described herein, embodiments of the described invention include a gas analyzer configured for accurate measurement of a level of a component gas present in a sample. More specifically, the gas cell utilizes a substantially collimated beam and mirrors configured to substantially eliminate reflections within the gas cell.

Figure 2:
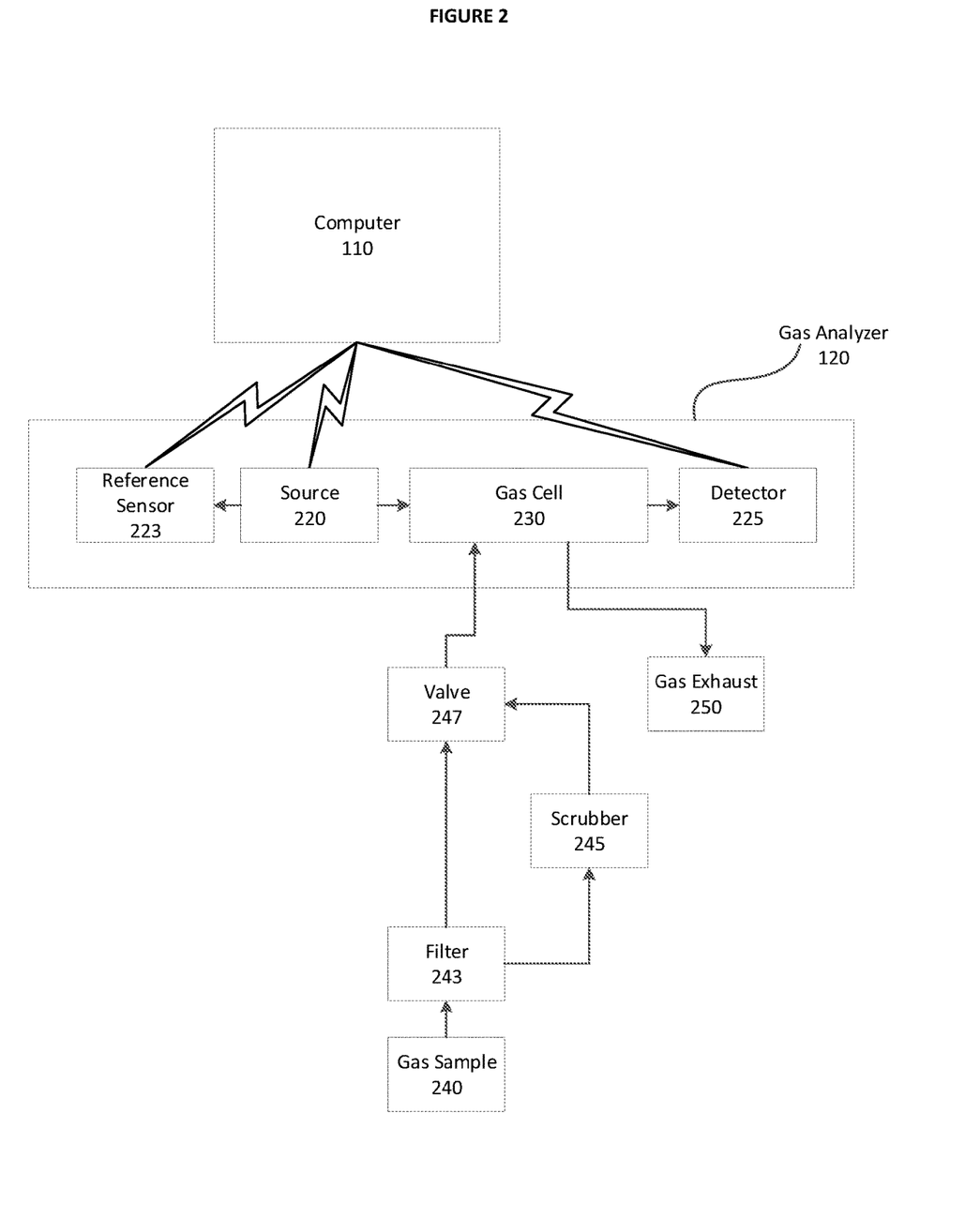
FIG. 2 is a functional block diagram of one embodiment of the gas analyzer instrument of FIG. 1 with a gas cell and a source.

FIG. 2 provides a functional block diagram illustrating an example of gas analyzer 120 of FIG. 1 that includes detector 225, source 220, and reference sensor 223 in communication with computer 110. The example of FIG. 2 also illustrates gas analyzer 120 that includes gas cell 230 configured to receive gas sample 240 via valve 247. Those of ordinary skill in the art appreciate that valve 247 may, for example, include a 3-way valve that may be under operational control of computer 110 (not shown), a microcontroller, or other control element. In the presently described example, valve 247 may be configured to select the flow path of gas sample 240 where a first flow path may be configured to direct gas sample 240 from a source (e.g. an intake from the surrounding environment, smoke stack, etc.) through filter 243 that may be configured to remove particulate material, to gas cell 230. Further, a second flow path may be configured to direct gas sample 240 from the source through filter 243 to scrubber 245 that may be configured to substantially remove one or more gas components of gas sample 240 (e.g. create "zero air"), then on to gas cell 230. Valve 247 may alternate between the first flow path and the second flow path at a set interval (e.g. a 10 second interval) or at a variable interval. For instance, the interval should be long enough to ensure that either unfiltered gas sample 240, or filtered "zero air" completely flushes gas cell 230 for an accurate measurement. A shorter time interval provides the benefit of an increased data collection rate and faster time response. The time interval may also be dependent, at least in part, on a rate of exhaust through gas exhaust 250 (described below).

FIG. 2 also illustrates gas exhaust 250 coupled to gas cell 230 which may be configured to facilitate removal of gas sample 240 from gas cell 230. For example, gas exhaust 250 may include one or more elements that creates a vacuum that may be used to draw gas sample 240 through gas cell 230 (e.g. a vacuum pump, etc.). In the presently described example, gas exhaust 250 may then vent gas sample to 240 to the environment or send gas sample 240 to another element for safe treatment and handling of gas sample 240.

As described above, FIG. 2 illustrates gas analyzer 120 with detector 225, which may include any type of detector known in the related art. For example, detector 225 may include a photomultiplier, a photodiode, a CCD, or other type of detector.

Further, gas analyzer 120 includes source 220, which may include any source know in the related art configured to produce a substantially collimated beam. For example, the substantially collimated beam comprises a very narrow band width and with a very narrow diverging angle such that there is essentially no loss of energy from the beam as it travels along a beam path. Also, importantly the described embodiments of source 220 may remove the need to include a band pass filter in the optical design, where a typical band pass filter is used to remove unwanted wavelengths of light from the beam. In the presently described example, source 220 may include an LED that produces a beam with a peak value of about 405 nm, a band width of about 10 nm, and a diverging angle of less than 15 degrees.

Also in the same or alternative embodiments, the light produced from source 220 may be modulated (e.g. operated in a pulse mode) in order to significantly minimize the degree of decay that can reduce the life expectancy of source 220. The modulation may also promote a high level of performance of gas analyzer 120 (e.g. achieve a detection limit of about 1 ppb, or sub ppb level). For example, source 220 may include an LED with a modulation rate of about 1000 Hz.

FIG. 2 also illustrates reference sensor 223 configured to detect changes in an energy level of light emitted from source 220 and located in a position that enables detection of light from source 220. Some embodiments of source 220 may produce more than one output beam, a first beam in one direction with a high level of energy and a second beam in a second direction that may be in a substantially opposite direction from the first beam where the second beam has a lower level of energy when compared to the first beam (e.g. <1% of the energy of the first beam). Reference sensor 223 may include any type of sensor known in the art. For example, reference sensor 223 may include a photodiode positioned in close proximity to source 220 where the position enables reference sensor 223 to receive output of a second beam from source 220.

Figure 3:
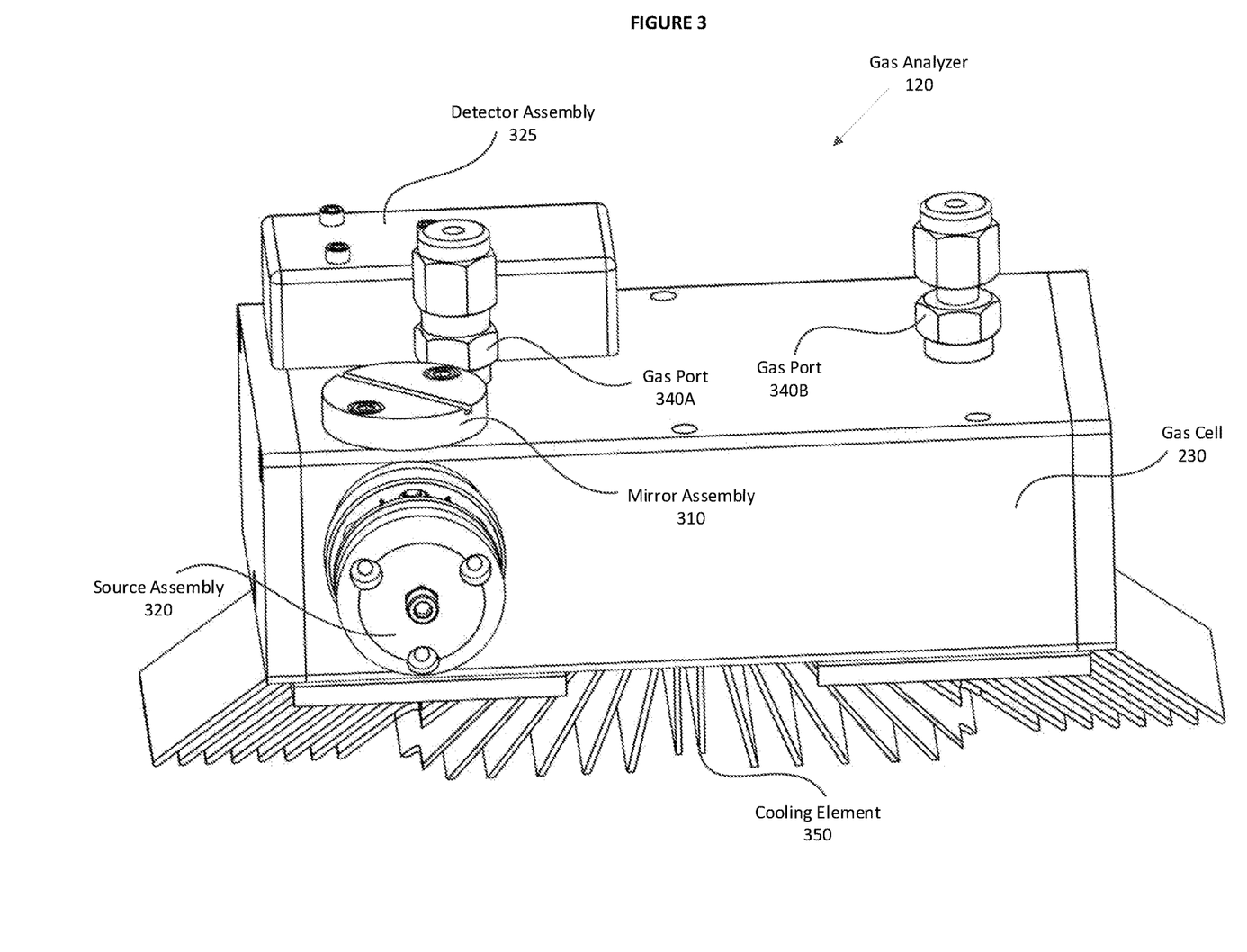
FIG. 3 is a simplified graphical example of one embodiment of the gas analyzer instrument of FIGS. 1 and 2 with a source assembly and a detector assembly.

FIG. 3 provides an illustrative example of an outside view of gas analyzer 120 that include detector assembly 325 configured to house detector 225, source assembly 320 configured to house source 220, mirror assembly 310 configured to support turning mirror 420A (described below), gas ports 340A and 30B configured to introduce and remove gas sample 240 from gas cell 230 (e.g. they could be used interchangeably), and cooling element 350 that may include fins configured to disperse heat from gas analyzer 120. Importantly, gas analyzer 120 is very compact when compared to previously known analyzers making gas analyzer 120 portable as well as more easily positioned in locations with space constraints.

Figure 4A:
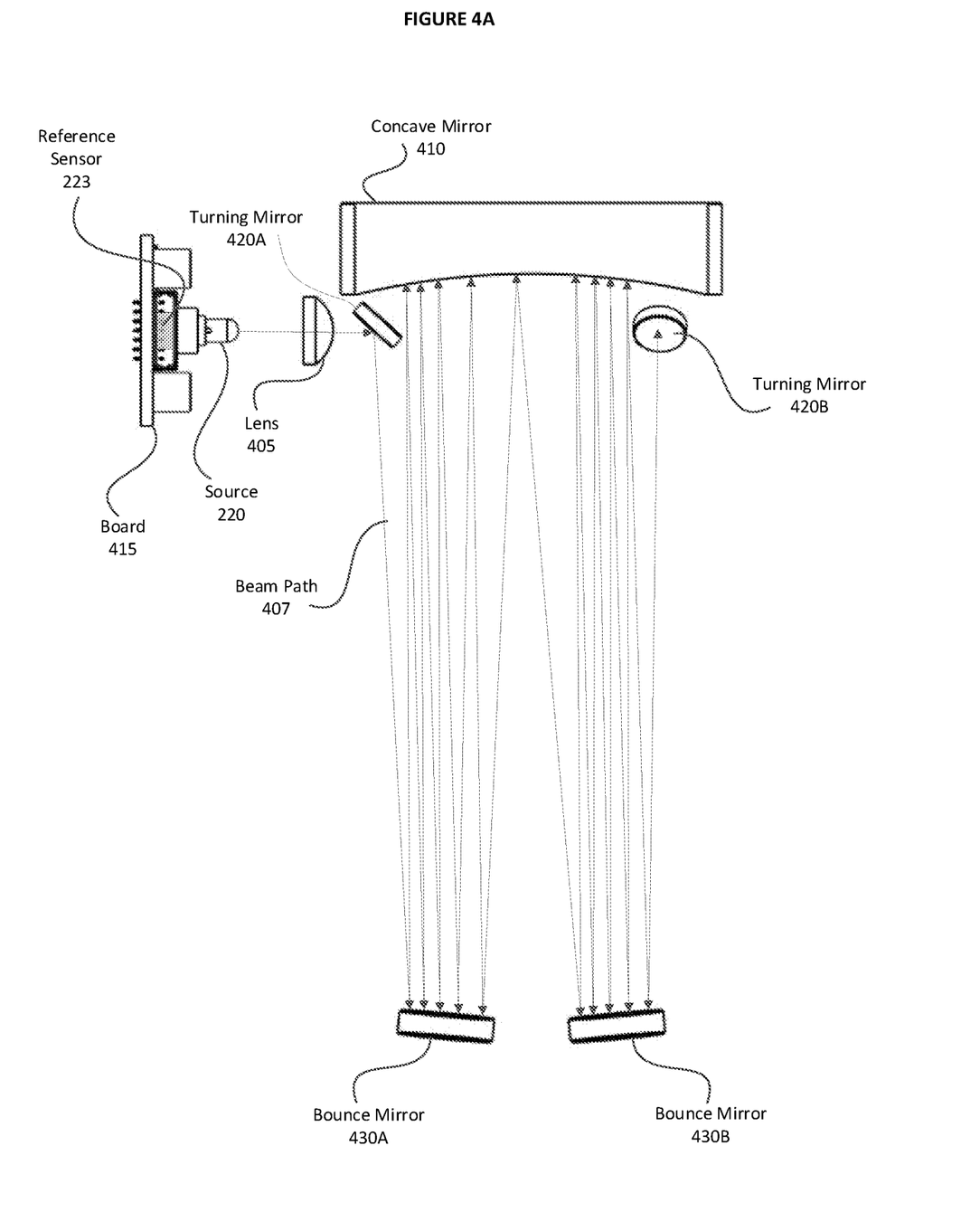
FIG. 4A is a simplified graphical example of one embodiment of the source of FIG. 2 with a producing a beam path guided by a plurality of mirrors.

FIG. 4A provides an illustrative example of a view of elements within gas cell 230 (e.g. a "top view" without housing). Source 220 produces a substantially collimated beam along beam path 407 that travels through lens 405 that focuses the beam such that the diverging angle remains completely within the reflective area of the mirrors 420A, 430A, 410, 430B, and 420B. In some cases, lens 405 further collimates the beam to substantially decrease the possibility of energy loss from the beam (e.g. energy losses may be limited to the mirror surfaces and/or absorption by gas sample 240).

Beam path 407 then reflects off turning mirror 420A, then reflects multiple times off each of bounce mirror 430A, concave mirror 410, and bounce mirror 430B. Importantly, bounce mirror 430A, concave mirror 410, and/or bounce mirror 430B may refocus the beam to the next element at each reflection to minimize the potential for loss of energy (e.g. that may reflect off the walls of gas cell 230 creating interference from water). Also, bounce mirror 430A, concave mirror 410, and/or bounce mirror 430B may have a coating that substantially improves the efficiency of reflection. In some embodiments, the coating may include a dielectric coating configured to provide greater than 99% reflectivity of a substantially collimated beam. For example, beam path 407 may include a large number of reflections in order to increase the path length and thus increase the exposure of the light beam to gas sample 240 while at the same time substantially eliminating interference signals produced from water. In the presently described example, gas cell 230 may include a path length of at least 2 meters which contributes to the ability to achieve a detection limit of about 1 ppb, or sub ppb level. Further, the presently described invention is configured to enable a very fast response time to identify an amount of a gas component after introduction of sample gas 240 into gas cell 230 (e.g. about 10 seconds or less).

Figure 4B:
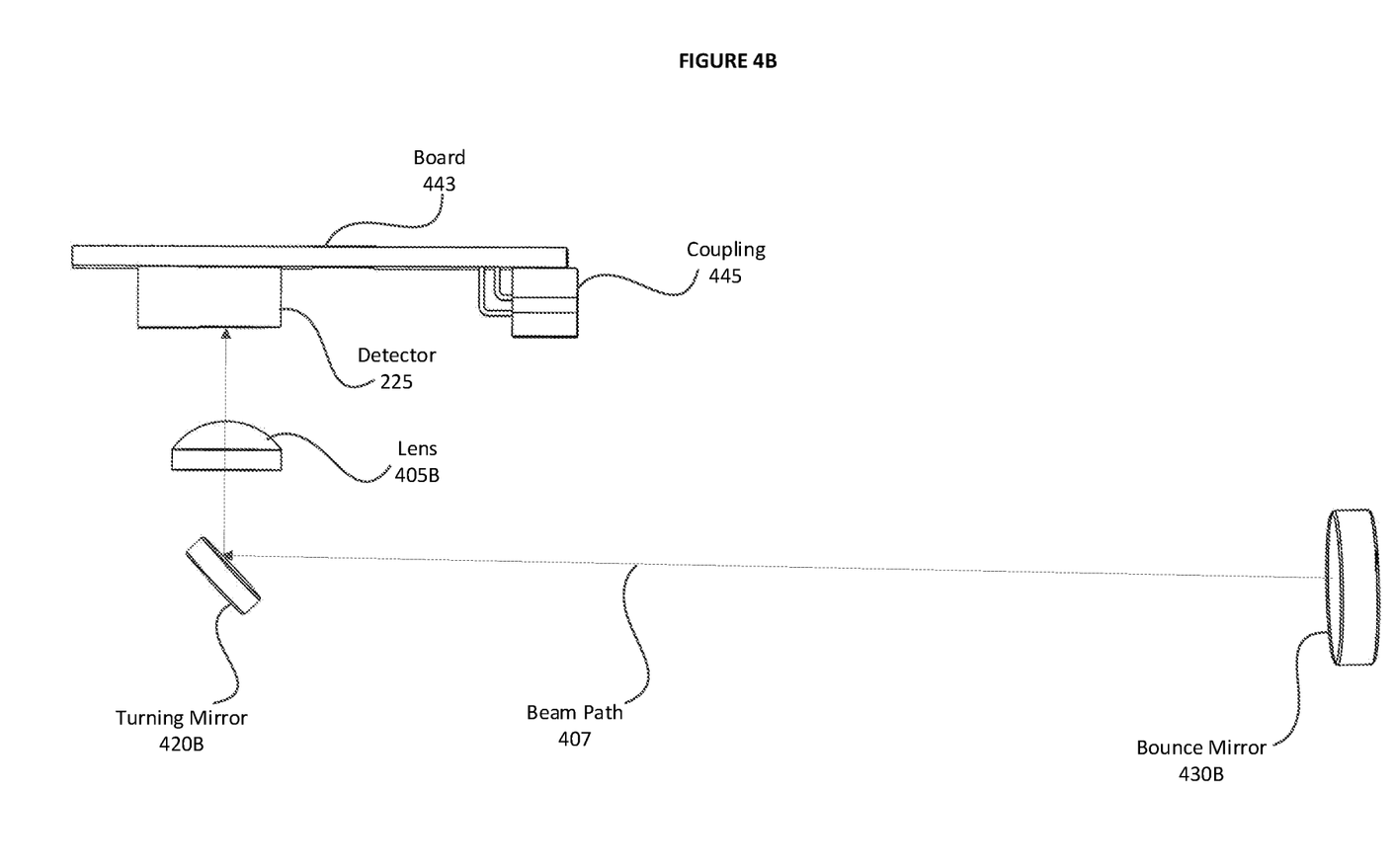
FIG. 4B is a simplified graphical example of one embodiment of the beam path of FIG. 4A directed to a detector via a mirror.

FIGS. 4A and 4B further illustrates turning mirror 420B that reflects the substantially collimated beam traveling along beam path 407. For example, FIG. 4B provides an illustrative example of beam path 407 reflecting off turning mirror 420B in a direction that is substantially orthogonal to beam path 407 from bounce mirror 430B to turning mirror 420B (e.g. in an "upward" direction), through lens 405B that focuses the substantially collimated beam to detector 225 (e.g. to the active area of detector 225 positioned at the focal point of lens 405B to maximize the collection efficiency of light). In the example of FIG. 4B, detector 225 is attached to board 443 that may include a PCB that communicates signals from detector 225 through coupling 445.

Turning back to the example FIG. 4A, source 220 is attached to board 415, that may include a PCB. Reference sensor 223 may also be mounted on board 415 and positioned in close proximity to and directly opposite from the direction of a first beam along beam path 407 produced by source 220. For example, source 220 produces a second beam in a direction that is opposite from the direction of a first beam, where the first beam includes a substantially higher power level compared to the second beam.

In some embodiments, reference sensor 223 may be employed to measure changes in the amount of energy produced by source 220. For example, the amount of energy produced by source 220 may fluctuate with changes in temperature that can affect the accuracy of detection of gas analyzer 120 (e.g. the fluctuation may be equal in both the first and second beams from source 220). In the presently described example, computer 110 may receive signals from reference sensor 223 to identify any changes in the amount of energy produced by source 220. In response to changes, computer 110 may use one or more temperature control elements (e.g. a thermoelectric cooler (TEC)) to maintain the temperature of source 220 to within a desired range about a set point (e.g. the desired range may include a range of about 0.1 Kelvin about a set point of about 25° C.).

It will be appreciated that any range and any set point may be used, and in some cases the set point may be selectable by user 101 or the set point may be substantially the same as the ambient environment surrounding gas analyzer 120. For example, the specific temperature set point may not impact the accuracy of gas analyzer so long as the temperature fluctuation of source 220 is kept within the desired range. In some cases, to minimize the amount of energy used by the temperature control elements it may be desirable that the set point is substantially the same as the ambient temperature of the environment outside of gas analyzer 120. In such a case the set point may be selected by user 101, and/or a temperature sensor may be used to measure the ambient temperature that can then be used as the set point.

Figure 5:
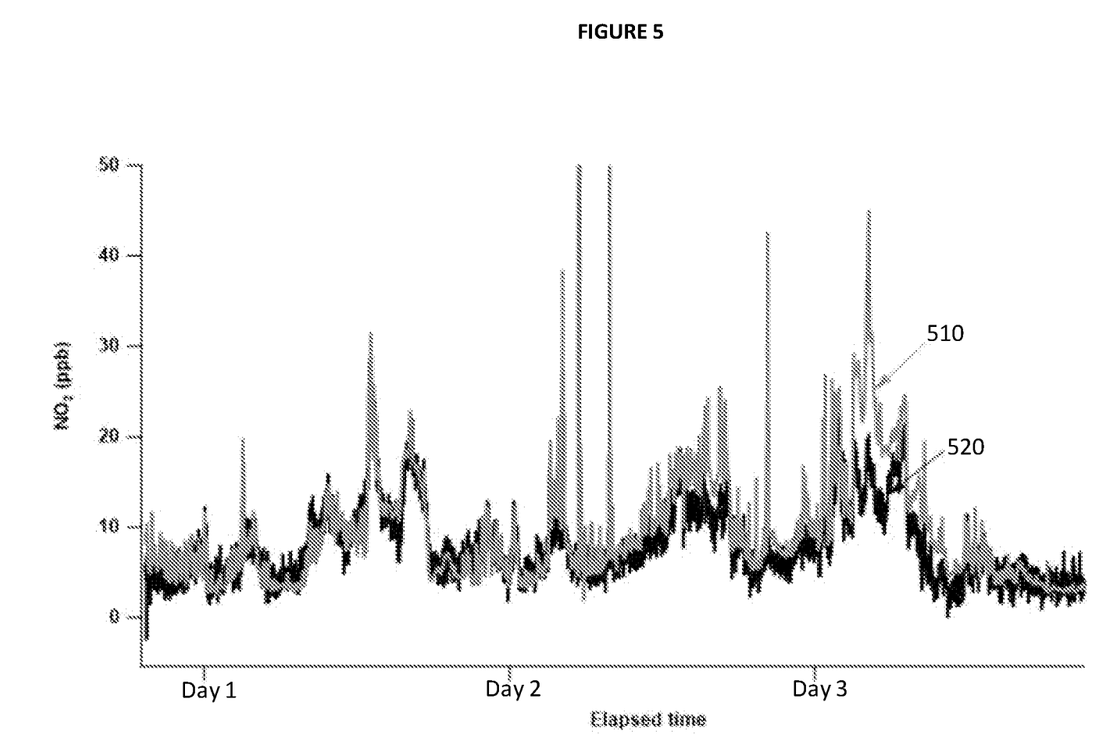
FIG. 5 is a simplified graphical example of one embodiment of a comparison of data collected using the gas analyzer of FIGS. 1-3, 4A, and 4B.

FIG. 5 provides an illustrative example of a comparison of results obtained from an existing instrument (e.g. 42iQ instrument from Thermo Fisher Scientific) and an embodiment of the presently described invention (e.g. portable gas analyzer). As illustrated in FIG. 5, the embodiment of the presently described invention produced trace 520 that achieved a lower limit of detection than the existing instrument that produced an overestimation as illustrated by trace 510.

Having described various embodiments and implementations, it should be apparent to those skilled in the relevant art that the foregoing is illustrative only and not limiting, having been presented by way of example only. Many other schemes for distributing functions among the various functional elements of the illustrated embodiments are possible. The functions of any element may be carried out in various ways in alternative embodiments

What is claimed is:

1. A gas analyzer, comprising:
    an LED light source attached to a board and configured to produce a substantially collimated first beam with a first level of energy and a small diverging angle, and a second beam comprising a second level of energy that is different from the first level of energy;
    a reference sensor mounted to the board adjacent to the LED light source, wherein the reference sensor detects the second level of energy of the second beam;
    a processing system configured to compensate for variation in the level of energy of the substantially collimated first beam using the detected level of energy of the second beam, wherein the variation of the first and second energy levels is substantially equal and associated with temperature fluctuation of the LED light source;
    a gas cell comprising an inlet configured to introduce a gas into the gas cell, an outlet configured to remove the gas from the gas cell, a first lens, a plurality of mirrors configured to reflect the substantially collimated first beam within the gas cell, and a second lens; and
    a detector configured to generate a signal in response to the substantially collimated first beam.

2. The gas analyzer of claim 1, wherein:
    each of the mirrors is configured to re-focus the reflected substantially collimated first beam.

3. The gas analyzer of claim 1, wherein:
    an energy level of the substantially collimated first beam at the detector is substantially equal to an energy level of the substantially collimated first beam produced by the light source.

4. The gas analyzer of claim 1, wherein:
    each of the mirrors comprises a dielectric coating configured to provide greater than 99% reflectivity of the substantially collimated first beam.

5. The gas analyzer of claim 1, wherein:
    the substantially collimated first beam comprises a band width of about 10 nm.

6. The gas analyzer of claim 1, wherein:
    the substantially collimated first beam comprises a peak value of about 405 nm.

7. The gas analyzer of claim 1, wherein:
    the gas cell comprises a pass line distance of about 2 meters.

8. The gas analyzer of claim 1, wherein:
    the substantially collimated first light beam is reflected about 20 times in the gas cell.

9. The gas analyzer of claim 1, wherein:
    the LED light source produces the second beam in an opposite direction from the substantially collimated first beam.

10. The gas analyzer of claim 1, wherein:
    the second level of energy comprises a small level of energy compared to the first level of energy.

11. The gas analyzer of claim 1, further comprising:
    a thermo electric cooler configured to maintain the temperature of the LED light source, wherein the processing system provides instruction to the thermo electric cooler to compensate for the variation in the level of energy of the substantially collimated first beam.

12. The gas analyzer of claim 11, wherein:
    the processing system maintains a range of temperature of the LED light source around a set temperature, wherein the set temperature is selectable.

13. The gas analyzer of claim 12, further comprising:
    a temperature sensor configured to detect an ambient temperature, wherein the set temperature comprises the ambient temperature.

14. The gas analyzer of claim 1, wherein:
    wherein the first lens is configured to focus the first beam so that diverging angle remains substantially within a reflective area of each of the mirrors.

15. The gas analyzer of claim 1, wherein:
    wherein the second lens is configured to produce a focal point on an active area of the detector to maximize the collection efficiency of light.

16. The gas analyzer of claim 1, wherein:
    wherein the small diverging angle is less than about 15 degrees.

* * * * *

UNITED STATES PATENT AND TRADEMARK OFFICE
CERTIFICATE OF CORRECTION

| | |
|---|---|
| PATENT NO. | : 12,000,774 B2 |
| APPLICATION NO. | : 17/823200 |
| DATED | : June 4, 2024 |
| INVENTOR(S) | : Yongquan Li, Brian Chia and Robert Bailey |

It is certified that error appears in the above-identified patent and that said Letters Patent is hereby corrected as shown below:

On the Title Page

In Column 1, item (72), in Inventors, Line 1, delete "Schenactady," and insert -- Schenectady, --, therefor.

Signed and Sealed this
Third Day of September, 2024

Katherine Kelly Vidal
*Director of the United States Patent and Trademark Office*